United States Patent [19]
Stewart

[11] Patent Number: 5,168,763
[45] Date of Patent: Dec. 8, 1992

[54] METHOD AND APPARATUS FOR COLLECTING COREFLOOD FLUIDS

[75] Inventor: David P. Stewart, Littleton, Colo.

[73] Assignee: Marathon Oil Company, Findlay, Ohio

[21] Appl. No.: 629,281

[22] Filed: Dec. 17, 1990

[51] Int. Cl.$^5$ .................................................. G01N 1/18
[52] U.S. Cl. .................................. 73/863.45; 73/864; 141/130; 141/131
[58] Field of Search ............... 73/38, 863.41, 863.45, 73/863.51, 863.52, 863.53, 863.56, 864, 864.73, 864.51, 864.25, 153; 141/130, 131

[56] References Cited

U.S. PATENT DOCUMENTS 2,355,620  2/1942  Bower et al. .................. 141/130
3,924,471  12/1975  Singer .......................... 141/130 X

FOREIGN PATENT DOCUMENTS 730248  8/1932  France .......................... 73/863.45

Primary Examiner—Hezron E. Williams
Assistant Examiner—Michael Brock
Attorney, Agent, or Firm—Jack L. Hummel; Jack E. Ebel

[57] ABSTRACT

A method and means for delivering the liquid generated by a coreflood experiment to test tubes and the gas so generated to a gas outlet. A mixture of gas and liquid is fed through an axially rotating tube extending through the central portion of a sealed chamber in which the test tubes are arranged in a circular path. The tube has a transversely extending delivery portion which deposits liquid into the test tubes, while gas is collected through a conduit leading from the chamber. The tube is incrementally rotated through a mechanism which allows fluid from the core sample to flow into the tube at the same back pressure under which the experiment takes place.

12 Claims, 3 Drawing Sheets

METHOD AND APPARATUS FOR COLLECTING COREFLOOD FLUIDS

FIELD OF THE INVENTION

This invention relates to the collection of fluids generated during coreflood experiments. More particularly, it relates to a method and apparatus for collecting fluids under the back pressure conditions existing during such experiments.

BACKGROUND OF THE INVENTION

Core samples from subterranean hydrocarbon formations are routinely tested for permeability and to determine the flow characteristics of possible flooding operations in such formations. In running coreflooding experiments, the sample is first saturated with a liquid such as oil, then placed in a sample holder where it is exposed to a pressurized fluid. The pressurized fluid, which may be gas, such as helium, or a liquid, such as a foam, displaces the saturating liquid, and the fluid mixture is then collected and separated into its liquid and gaseous components for measurement and analysis.

Automated gas-liquid permeameters have been developed for continuously collecting and instantaneously measuring produced fluids, but these are relatively expensive and not always available for use. More often, the produced fluids from coreflooding experiments run under back pressure are incrementally collected by one of two methods. One method requires fluid to be collected at atmospheric pressure downstream of the back pressure regulator in the system. Under these conditions both the liquid and gas phases of the fluid pass through the back pressure regulator which, due to the varied viscosities of the liquids, gases and emulsions passing through, tends to repeatedly build and release pressure. As a result, the pressure in the system fluctuates during a test procedure, which lessens the accuracy of pressure measurements.

In another method all the liquid phases are collected prior to the fluid reaching the back pressure regulator, allowing only the gas phase to pass through the back pressure regulator. The gas phase is then collected downstream of the back pressure regulator or at atmospheric pressure. The collected liquid and gas phases can then be separately measured and analyzed. A problem that can be encountered in this method, depending on the particular test equipment involved, is that the production tube that delivers liquid to the collection receptacles is often required to be so long that it interferes with the operation of the stepper motor employed to sequentially align the production tube and the collection receptacles. Another problem is the need to minimize production dead volume in test equipment employed in carrying out this method.

It is therefore an object of the present invention to overcome these problems by providing an improved mechanical arrangement for delivering and collecting fluid from a coreflood sample under back pressure conditions.

BRIEF SUMMARY OF THE INVENTION

In accordance with the invention, a plurality of receptacles are provided with their open ends spaced from each other and disposed along a substantially circular arc. A fluid delivery tube comprising a central portion and a transversely extending delivery portion is provided, with the central portion having an axis substantially aligned with the center of rotation of the circular arc and with the end of the delivery portion of the tube overlying the receptacles lying on the circular arc. The delivery tube is mounted for rotation about the axis of the central portion. A sealed chamber is in communication with the open ends of the receptacles, and the delivery portion of the tube is movable through the chamber upon rotation of the tube. By incrementally rotating the delivery tube about the axis of its central portion, the end of the tube is able to deliver fluid to each of the receptacles in turn. The chamber may also be provided with an outlet to gas collection means located outside the chamber, so that the liquid and gas components of fluid comprised of liquid and gas phases can be collected separately. This method, while of use in any experimental situation involving the collection of small volumes of fluids, is especially useful in collecting fluid resulting from driving saturating liquid from a core sample.

The means for rotating the delivery tube comprises a stationary element in which a rotatable element is mounted. The rotatable element is connected to the delivery tube so that rotation of the element results in rotation of the tube. Fluid is delivered to the rotating element through connecting bores in the stationary and rotatable elements. The rotatable element preferably extends through the stationary element where it is coupled to rotating means, such as the shaft of a stepper motor.

This arrangement is economical and highly efficient, permitting the fluid to be collected under back pressure conditions in a manner which eliminates the need for a long delivery tube and avoids or greatly reduces dead production volume.

The features of the invention which enable it to function in the desired manner are brought out in more detail in the following detailed description of the preferred embodiment, wherein the above and other aspects of the invention, as well as other benefits, will readily be apparent.

DETAILED DESCRIPTION OF THE PREFERRED EMBODIMENT

Figure 1:
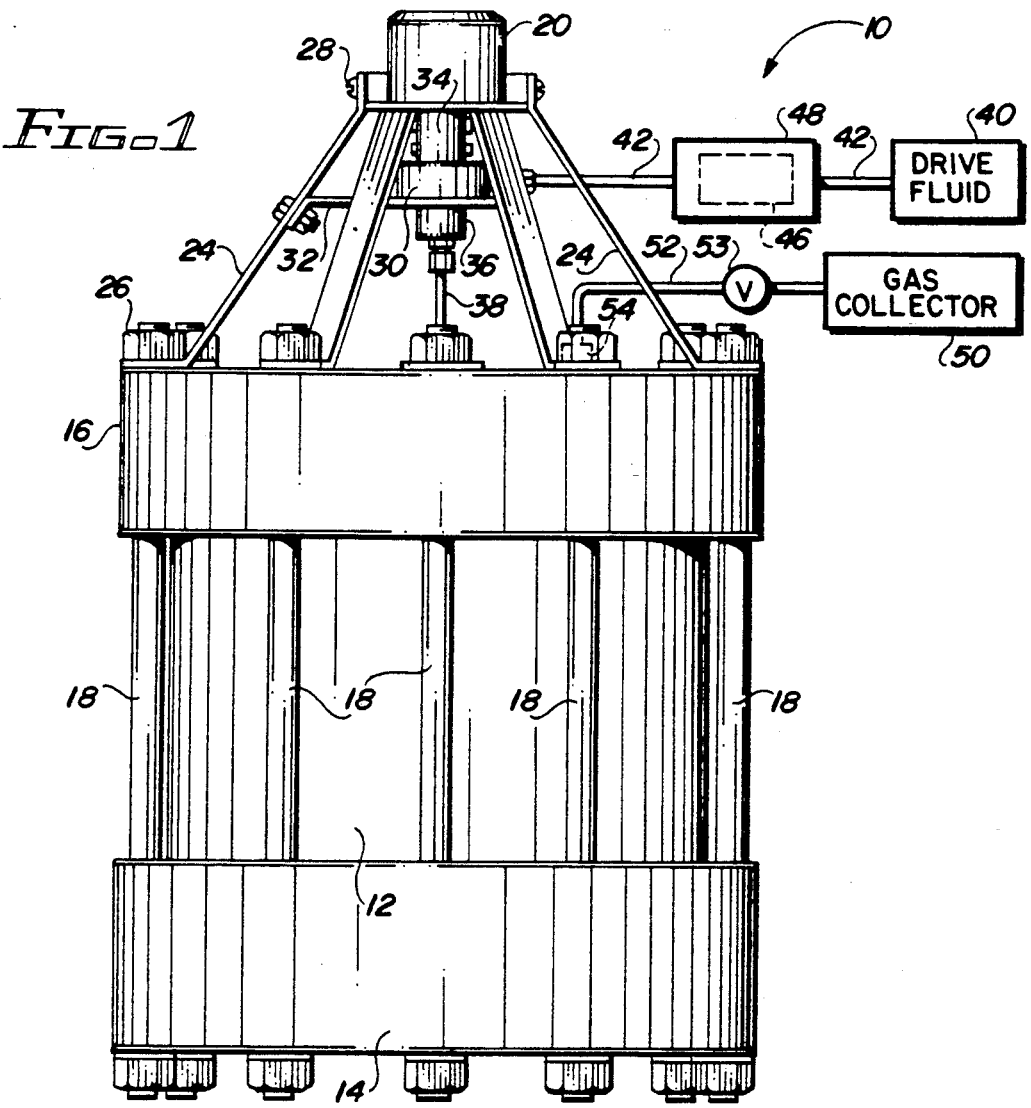
FIG. 1 is side elevation of the apparatus of the present invention, with portions of the flow lines being schematically shown.

Referring to FIG. 1, the fluid collecting apparatus 10 of the invention comprises a central block 12 clamped between a base 14 and an upper block or cap 16. The base and cap are of greater diameter than the central block, and are attached to each other by a series of tension rods 18 connected to portions of the base and upper block which extend laterally beyond the periphery of the central block. A stepper motor 20 is supported by plate 22 which in turn is supported above the upper block 16 by a plurality of braces or struts 24. The struts are attached to the upper block 16 by the nuts 26 which hold the threaded ends of the tension rods 18 in place, and to the support plate 22 by bolts 28. Intermediate the height of the struts 24, a stationary element 30 is supported on plate 32, and rotating elements 34 and 36 are mounted above and below the element 30 as described in more detail below. A fluid delivery tube 38 is connected to the rotating element 36 for rotation therewith, in order to deliver liquid and gas for collection as explained in detail below.

Still referring to FIG. 1, a source 40 of drive gas or liquid is connected by fluid line 42 to a core sample 46 mounted in the core sample holder 48. The holder may be of any convenient type, such as a conventional Hassler core holder. The fluid line 42 continues from the core holder 48 and is connected to the stationary element 30. Also illustrated is a gas collection device 50 which is connected to the apparatus by a tube 52 connected to the upper block 16 by connection 54. A back pressure regulator 53 is provided between the tube 52 and the gas collector 50. The back pressure regulator, which may be of any standard design such as a diaphragm type of regulator, maintains the desired pressure in the system, which in the case of a coreflood experiment may typically be in the order of 50 psig. In any case, the back pressure regulator should be capable of maintaining a maximum working pressure consistent with design and material limitations, such as, for example, in the order of 500 psig.

Figure 3:
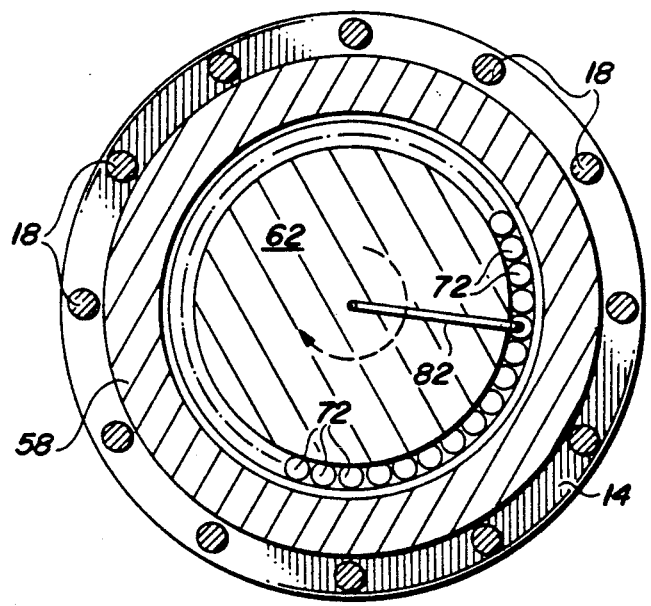
FIG. 3 is a transverse sectional view taken on line 3—3 of FIG. 2.
Figure 2:
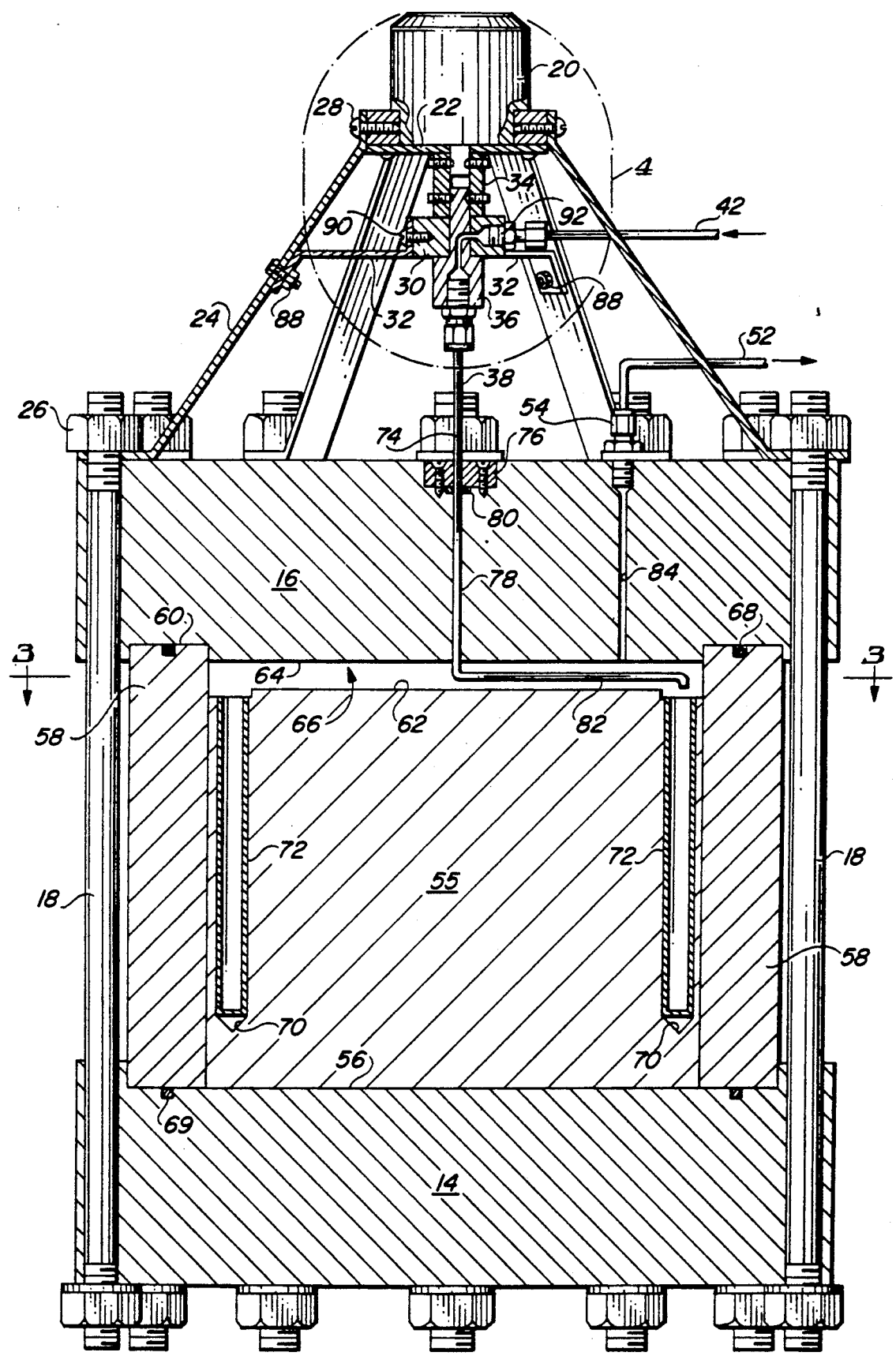
FIG. 2 is a longitudinal sectional view of the apparatus of FIG. 1.

The structure of the fluid collection area in the apparatus is shown in more detail in FIGS. 2 and 3. As illustrated, the central block 12 comprises a cylindrical insert 55, which rests in a recess 56 in the base 14 and is slidably mounted in a sleeve 58. The sleeve 58, which also rests in the recess 56, fits into a peripheral groove 60 in the upper block 16. The upper surface 62 of the insert 55 is spaced from the lower surface 64 of the upper block 16 to form, with the upper inner face portion of the sleeve 58, a chamber 66. The chamber 66 is sealed from the atmosphere by the 0-ring seal 68 in the upper surface of the sleeve and the 0-ring seal 69 in the upper surface of the base 14. Located in the insert 55 adjacent the periphery of the chamber 66 are bores 70 in which test tubes 72 reside. As best shown in FIG. 3, the test tubes are arranged in a circular path and are spaced from each other. The spacing may vary as desired, but for purposes of accuracy of measurement and the elimination or reduction of dead spots in the collection of liquid, it is preferred that they be closely spaced. The provision of a large number of test tubes, such as thirty-six, for example, has been found to be satisfactory.

Still referring to both FIGS. 2 and 3, the delivery tube 38 enters the upper block 16 through a bore 74 in an insert 76 mounted in a counterbore in the upper block. The insert bore 74 is aligned with a bore 78 in the upper block which allows the tube 38 to extend down from the rotatable member 36 to the chamber 66. A suitable bearing or Teflon washer 80 may be provided in a smaller counterbore at the base of the larger counterbore in the upper block 16 to facilitate rotation of the tube 38. The tube has a transverse delivery portion 82 in the chamber 66 terminating in an open end overlying the test tubes 72. The upper block 16 is further provided with a bore 84 leading from the chamber 66 to the conduit or tube 52 attached at the fitting 54. As mentioned previously, the tube 52 is connected to a gas collection device 50.

Figure 4:
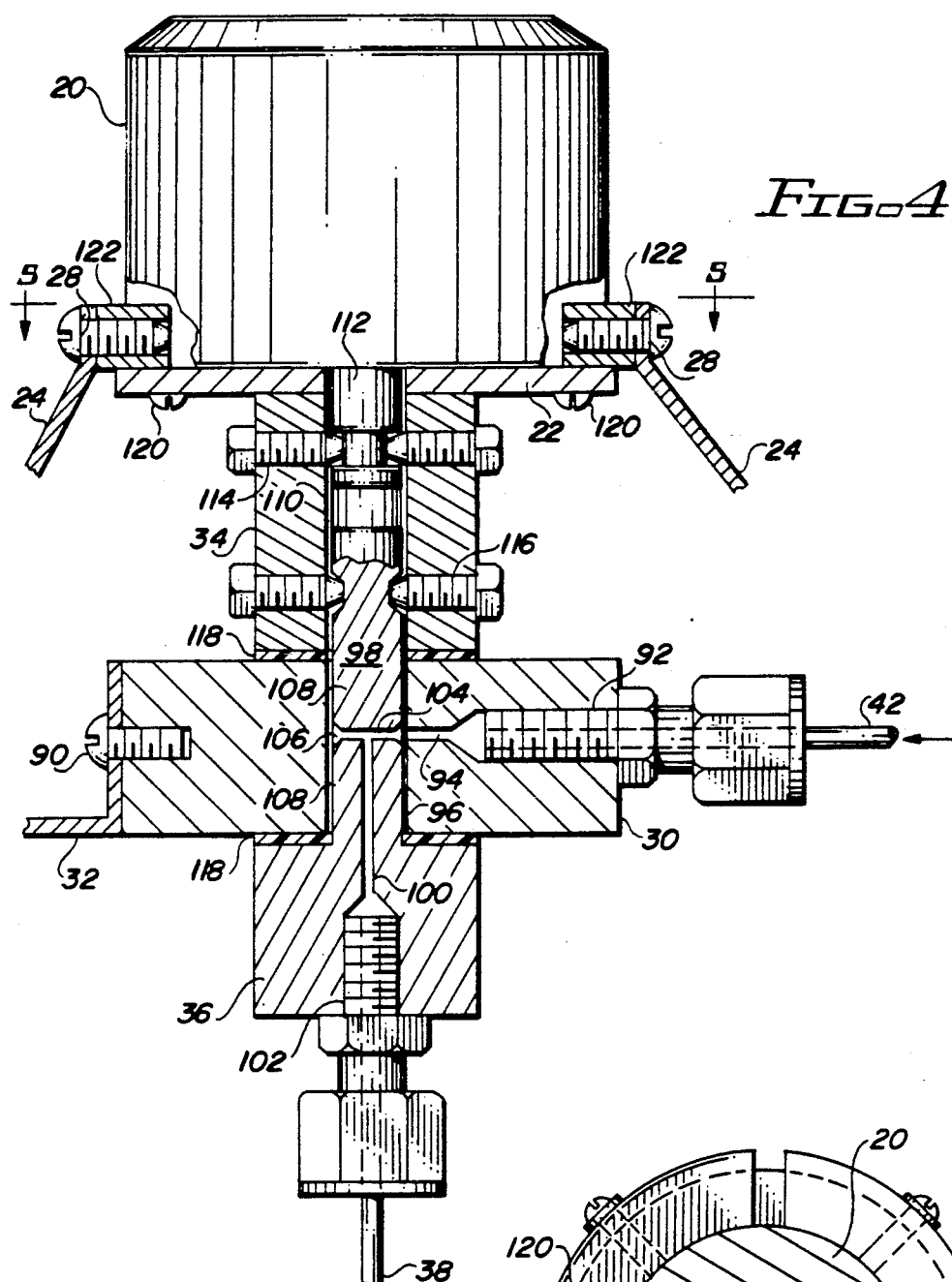
FIG. 4 is an enlarged longitudinal sectional view of the fluid connecting elements of FIG. 2.

Referring now to the upper portion of FIG. 2 and to FIG. 4, the outer end portions of two or more intermediate support plates 32 are attached by bolts 88 to two or more of the struts 24. The other end portions of the support plates 32 are attached by screws 90 to the stationary element 30, thereby supporting the element 30 at the desired height. A suitable fitting 92 connects the tube 42 to the stationary element 30. A bore 94 connects the fitting 92 to a bore 96 extending vertically through the central portion of the member 30.

The lower rotating element 36 has a vertical projection or shaft 98 which extends up through the bore 96 in the stationary member 30. The member 36 has a bore 100 extending from the fitting 102 to which the tube 38 is connected to one or more transverse bores 104. The transverse bores 104 extend from the end of the bore 100 to a V-groove 106 encircling the periphery of the projection 98, with the V-groove being located at the end of the bore 94. 0-rings 108 are provided on the projection or shaft 98 on either side of the V-groove 106 to prevent fluid from leaking out the bore 96, thereby causing all the fluid to flow through the bore 100 and into the tube 38.

The projection 98 of rotatable element 36 extends up beyond the stationary member 30 into the bore 110 of the rotatable sleeve 34, and the output shaft 112 of stepper motor 20 extends down through a central opening in the support plate 22 into the bore 110. The sleeve 34 is fixed to the shaft 112 by set screws 114 which engage a circumferential groove in the shaft 112, and to the projection 98 by set screws 116 which engage a circumferential groove in the projection 98. Washers 118, made of low friction material such as Teflon, are provided between the sleeve 34 and the stationary member 30 and between the stationary member and the rotatable member 36 to facilitate rotation of the sleeve and rotatable member.

Figure 5:
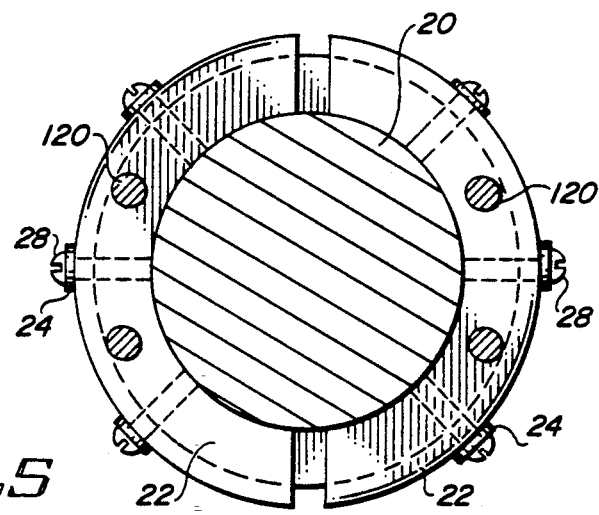
FIG. 5 is a transverse sectional view taken on line 5—5 of FIG. 4.

As best shown in FIGS. 2, 4 and 5, the stepper motor 20 is supported by and attached to the plate 22 by screws 120. The base of the motor is surrounded by two half-collars 122 which are secured to the support plate 22 by means of the screws 120 extending through openings in the half-collars. Through this arrangement, the struts 24 are effectively connected to the support plate by means of the screws 28 connecting the struts to the half-collars 122. The motor can thus be quickly set in place and securely held in stationary position during operation.

Referring to FIG. 1, in operation a core sample 46 saturated with suitable liquid is placed in the core holder 48, and gas or other driving fluid is introduced under pressure to the core holder. The resulting fluid, which may at this point consist of a mixture of liquid and gas phases and possibly emulsions, enters the tube 42 under the back pressure of the system. As best shown in FIGS. 2 and 4, the fluid passes through the bore 94 in the stationary element 30 into the V-groove in the projection 98, and from there through the lateral bores 104 to the axial bore 100. Flow continues through the fitting 102 into the tube 38.

As the stepper motor causes the shaft 112 to incrementally rotate, the connection of the sleeve 34 to the shaft 112 causes the sleeve to move correspondingly. Because the sleeve is also connected to the projection 98, the projection and integral member 36 are caused to rotate in a similar manner, thus causing the tube 38 to rotate with the element 36. As the upper vertical portion of the tube rotates, the lower transversely extending portion 82 is caused to rotate in step-by-step fashion about a point aligned with the axis of the tube 38. The operation of the stepper motor and the placement of the test tubes 72 are such that movement of the end of the tube portion 82 stops at a point overlying the next test tube in its path. Because the volume of liquid deposited in the test tubes is small (the capacity of each tube may, for example, be 10 ml) and the spacing between tubes is minimal, and because the rate of movement of the tube end is relatively great due to the relatively long transverse tube portion 82, very little liquid, if any, is lost during travel of the tube end to the next test tube. It will be understood that the tube end overlies each test tube for a relatively long period of time between each activation of the stepper motor while the test tube is being filled. Any gas in the fluid dispensed by the tube 82 will collect in the chamber 66 and exit through the bore 84 and the collection tube 52 to gas measurement and analysis means 50.

Although not shown, it will be understood that the stepper motor may be controlled by a suitable computer program.

It will now be apparent that the invention enables collected liquids to be maintained under constant pressure consistent with the pressure of the fluid exiting from the core sample, and allows collection of a volume of the liquid phase of the produced fluid as a function of time, as well as providing for simultaneous analysis of the gas phase volume as a function of time.

By collecting fluid in a sealed chamber the system pressure is maintained. Collection in the chamber is made possible by the manner of rotating the delivery tube about the center of the circular array of test tubes. The mechanical connections permitting the delivery of fluid under pressure to a rotating tube are simple yet highly efficient, and the relatively few components of the apparatus are capable of rapid assembly.

It should now be appreciated that the invention need not necessarily be limited to all the specific details of the described preferred embodiment, but that changes to certain features which do not alter the overall basic function and concept of the invention may be made without departing from the spirit and scope of the invention defined in the claims.

What is claimed is:

1. In apparatus for delivering fluid to a plurality of spaced receptacles arranged in a circular path:
    a stationary element having a bore adapted to be connected to a source of fluid to be measured;
    a rotatable element mounted in the stationary element for rotation about an axis substantially aligned with the center of rotation of said circular path, the rotatable element containing a bore in fluid communication with the bore in the stationary element;
    a fluid delivery tube having a central portion connected to the rotatable element in fluid communication with the bore therein;
    the fluid delivery tube also having a delivery portion extending transversely of the central portion thereof, the delivery portion terminating in an end overlying said circular path; and
    means for incrementally rotating the rotatable element so that the end of the delivery tube incrementally moves from one receptacle to the next.

2. The apparatus of claim 1, wherein a portion of the rotatable element extends through the stationary element and wherein the means for incrementally rotating the rotatable element includes a rotatable shaft, the apparatus further including means for connecting said portion of the rotatable element to the rotatable shaft and means for causing the rotatable shaft to rotate in incremental movements.

3. The apparatus of claim 2, wherein the means for connecting said portion of the rotatable element to the rotatable shaft comprises a sleeve having opposite ends receiving said rotatable element portion and the rotatable shaft, and means attaching the sleeve to said rotatable element portion and the rotatable shaft.

4. The apparatus of claim 3, wherein the portion of the rotatable element extending through the stationary element and into the sleeve comprises a shaft and wherein the stationary element includes a bore through which said portion extends, the apparatus further including sealing means between said shaft and said bore on both sides of the point at which the fluid bore in the rotatable element and the fluid bore in the stationary element connect.

5. Apparatus for delivering and collecting fluid to be measured, comprising:
    a housing;
    a plurality of spaced fluid receptacles in the housing having open ends located along a substantially circular arc;
    the housing containing a chamber communicating with the open ends of the receptacles;
    a fluid delivery tube adapted to be connected to a pressurized fluid source and being mounted for rotation in said chamber about an axis substantially aligned with the center of rotation of the circular arc, the tube having an open end adapted to overlie the open ends of the receptacles;
    means for rotating the delivery tube so that the open end thereof incrementally moves from one receptacle to the next;
    a conduit connecting the chamber to gas collection means;
    a back pressure regulator for controlling the pressure in the conduit; and
    means for sealing the chamber against atmospheric pressure.

6. A method for delivering and collecting fluid to be measured, comprising the steps of:
    providing a plurality of receptacles having open ends spaced from each other and disposed along a substantially circular arc;
    providing a delivery tube comprising a central portion having an axis substantially aligned with the center of rotation of the circular arc and a transversely extending delivery portion terminating in an end overlying the circular arc, the delivery tube being mounted for rotation about the axis of the central portion thereof;
    providing a sealed chamber communicating with the open ends of the receptacles, the delivery portion of the delivery tube being movable through the chamber upon rotation of the delivery tube;
    causing pressurized fluid comprised of a liquid component and a gas component to flow through the delivery tube;
    incrementally rotating the delivery tube about its central portion so as to move the end of the tube from one receptacle to another, thereby delivering the liquid component of the fluid to the receptacles; and
    collecting the gas component of the pressurized fluid in gas collection means located outside the chamber by providing a conduit connecting the sealed chamber to the gas collection means, the pressure of the gas component causing the gas component to flow through the conduit to the gas collection means.

7. The method of claim 6, wherein the fluid is obtained by providing a core sample saturated with liquid and driving the liquid from the core sample with pressurized fluid, the fluid delivered to the chamber comprising a mixture of liquid and gas.

8. The method of claim 6, wherein the pressure in the conduit is controlled by a back pressure regulator.

9. Apparatus for delivering and collecting fluid to be measured, comprising:
   a housing;
   a plurality of spaced fluid receptacles in the housing having open ends located along a substantially circular arc;
   the housing containing a chamber communicating with the open ends of the receptacles;
   a fluid delivery tube adapted to be connected to a fluid source and being mounted for rotation in said chamber about an axis substantially aligned with the center of rotation of the circular arc, the tube having an open end adapted to overlie the open ends of the receptacles;
   means for rotating the delivery tube so that the open end thereof incrementally moves from one receptacle to the next; and
   means for sealing the chamber against atmospheric pressure;
   the means for rotating the delivery tube including a rotatable element mounted in a stationary element for rotation about an axis substantially aligned with the axis of rotation of the fluid delivery tube, the rotatable element containing a bore in fluid communication with a bore in the stationary element, the bore in the stationary element adapted to be connected to a source of the fluid to be measured.

10. The apparatus of claim 9, wherein the rotatable element includes a projecting portion extending through the stationary element and being connected to a rotatable shaft, the apparatus further including means for causing the rotatable shaft to rotate in incremental movements.

11. Apparatus for delivering and collecting fluid to be measured, comprising:
   a housing;
   a plurality of spaced fluid receptacles in the housing having open ends located along a substantially circular arc;
   the housing containing a chamber communicating with the open ends of the receptacles;
   a fluid delivery tube connected to a fluid source comprising a core sample saturated with liquid and a drive fluid which forces the liquid from the core sample, the fluid delivery tube being mounted for rotation in said chamber about an axis substantially aligned with the center of rotation of the circular arc, the tube having an open end adapted to overlie the open ends of the receptacles and to deposit the liquid component of the fluid into the receptacles;
   a conduit connecting the housing chamber to gas collection means located outside the chamber, the conduit being adapted to receive the gaseous component of the fluid;
   means for rotating the delivery tube so that the open end thereof incrementally moves from one receptacle to the next; and
   means for sealing the chamber against atmospheric pressure.

12. A method for delivering and collecting fluid to be measured, comprising the steps of:
   providing a plurality of receptacles having open ends spaced from each other and disposed along a substantially circular arc;
   providing a delivery tube comprising a central portion having an axis substantially aligned with the center of rotation of the circular arc and a transversely extending delivery portion terminating in an end overlying the circular arc, the delivery tube being mounted for rotation about the axis of the central portion thereof;
   providing a sealed chamber communicating with the open ends of the receptacles, the delivery portion of the delivery tube being movable through the chamber upon rotation of the delivery tube;
   causing fluid to flow through the delivery tube; and
   incrementally rotating the delivery tube about its central portion so as to move the end of the tube from one receptacle to another, thereby delivering fluid to the receptacles;
   the delivery tube being rotated by connecting the delivery tube to a rotatable element mounted in a stationary element for rotation about an axis substantially aligned with the axis of rotation of the fluid delivery tube, providing a bore in the rotatable element in fluid communication with a bore in the stationary element, and connecting the bore in the stationary element to a source of the fluid to be measured.

* * * * *